United States Patent
Caleffi

(10) Patent No.: US 7,520,919 B2
(45) Date of Patent: Apr. 21, 2009

(54) TRANSDUCER-PROTECTOR DEVICE FOR MEDICAL APPARATUS

(75) Inventor: Luca Caleffi, Mirandola (IT)

(73) Assignee: Gambro Lundia AB, Lund (SE)

( * ) Notice: Subject to any disclaimer, the term of this patent is extended or adjusted under 35 U.S.C. 154(b) by 502 days.

(21) Appl. No.: 11/153,554

(22) Filed: Jun. 16, 2005

(65) Prior Publication Data

US 2005/0279692 A1    Dec. 22, 2005

Related U.S. Application Data

(60) Provisional application No. 60/522,627, filed on Oct. 21, 2004.

(30) Foreign Application Priority Data

Jun. 22, 2004    (IT)    .................. MO2004A0156

(51) Int. Cl.
*B01D 61/30* (2006.01)
*B01D 53/22* (2006.01)

(52) U.S. Cl. .................. 96/4; 96/6; 96/7; 96/421; 95/45; 95/46; 55/385.1; 55/502; 55/503; 55/511; 210/321.72; 210/321.75; 73/706; 604/5.01; 604/6.09; 285/226; 285/227

(58) Field of Classification Search ............ 96/4, 96/6, 7, 421; 95/45, 46; 55/385.1, 495, 502, 55/503, 511, DIG. 5; 210/321.6, 321.72, 210/321.75, 321.84, 445, 446; 73/706, 714; 604/4.01, 5.01, 6.09; 285/226, 227, 235

See application file for complete search history.

(56) References Cited

U.S. PATENT DOCUMENTS

| | | | |
|---|---|---|---|
| 3,831,588 A | 8/1974 | Rindner | |
| 3,932,153 A * | 1/1976 | Byrns | 55/511 |
| 4,047,526 A | 9/1977 | Reynolds et al. | |
| 4,056,116 A | 11/1977 | Carter et al. | |
| 4,077,882 A | 3/1978 | Gangemi | |
| 4,114,458 A | 9/1978 | Alinari | |
| 4,135,407 A | 1/1979 | Ezekiel | |
| 4,187,861 A | 2/1980 | Heffernan | |
| 4,209,013 A | 6/1980 | Alexander et al. | |
| 4,314,480 A * | 2/1982 | Becker | 73/706 |
| 4,412,834 A | 11/1983 | Kulin et al. | |
| 4,457,749 A | 7/1984 | Bellotti et al. | |
| 4,459,139 A * | 7/1984 | vonReis et al. | 96/6 |
| 4,475,914 A | 10/1984 | Portnoff | |

(Continued)

FOREIGN PATENT DOCUMENTS

DE    44 38 558 A1    5/1996

(Continued)

*Primary Examiner*—Jason M Greene
(74) *Attorney, Agent, or Firm*—Rissman Jobse Hendricks & Oliverio, LLP

(57) ABSTRACT

The transducer-protector device for medical apparatus comprises a housing formed by two half-shells, a membrane defining a gas-permeable anti-contamination barrier, a female Luer first connection port, a second connection port for connection to a flexible tube, a helical bellows-conformed deformable member. The device, which operates in a service line of an extracorporeal blood circuit associated to a dialysis machine, is for protecting the machine from contaminating agents originating from the circuit. The device is simple and economical to manufacture.

43 Claims, 4 Drawing Sheets

U.S. PATENT DOCUMENTS

| | | | |
|---|---|---|---|
| 4,541,283 A | 9/1985 | Stuhlmann | |
| 4,703,759 A | 11/1987 | Merrick et al. | |
| 4,773,458 A | 9/1988 | Touzani | |
| 4,832,317 A | 5/1989 | Alaphilippe | |
| 4,953,897 A * | 9/1990 | Klober | 285/226 |
| 5,024,220 A | 6/1991 | Holmgreen et al. | |
| 5,089,001 A | 2/1992 | Hwang | |
| 5,176,390 A | 1/1993 | Lallement | |
| 5,269,917 A * | 12/1993 | Stankowski | 210/232 |
| 5,372,491 A | 12/1994 | Fritsch et al. | |
| 5,443,723 A * | 8/1995 | Stankowski et al. | 210/321.75 |
| 5,458,586 A * | 10/1995 | Adiletta | 604/905 |
| 5,500,003 A * | 3/1996 | Guala et al. | 604/252 |
| 5,669,891 A | 9/1997 | Vaillancourt | |
| 5,676,346 A | 10/1997 | Leinsing | |
| 5,853,178 A | 12/1998 | Wydra et al. | |
| 6,029,946 A | 2/2000 | Doyle | |
| 6,048,335 A | 4/2000 | Mayer | |
| 6,168,653 B1 * | 1/2001 | Myers | 96/4 |
| 6,270,055 B1 | 8/2001 | Szeteli et al. | |
| 6,328,498 B1 | 12/2001 | Mersch | |
| 6,344,615 B1 | 2/2002 | Nolf et al. | |
| 6,541,802 B2 | 4/2003 | Doyle | |
| 6,578,878 B2 | 6/2003 | Berg | |
| 6,655,655 B1 | 12/2003 | Matkovich et al. | |
| 6,668,388 B2 | 12/2003 | Buttigieg | |
| 6,709,424 B1 | 3/2004 | Knierbein | |
| 7,069,788 B2 * | 7/2006 | Teugels | 73/706 |
| 7,175,697 B2 * | 2/2007 | Neri | 55/511 |
| D541,935 S * | 5/2007 | Mijers | D24/129 |

FOREIGN PATENT DOCUMENTS

| | | |
|---|---|---|
| EP | 0 395 758 | 11/1990 |
| EP | 0 404 361 | 12/1990 |
| EP | 0 497 229 | 8/1992 |
| EP | 0 652 018 A2 | 5/1995 |
| EP | 0 726 736 | 8/1996 |
| EP | 0 887 085 A2 | 12/1998 |
| EP | 0 925 799 | 6/1999 |
| EP | 0 974 473 | 1/2000 |
| EP | 1 236 482 | 9/2002 |
| FR | 2 452 653 | 10/1980 |
| FR | 2 742 196 | 6/1997 |
| WO | WO 96/00646 | 1/1996 |
| WO | WO 01/93936 | 12/2001 |
| WO | WO 02/05873 | 1/2002 |
| WO | WO 03/095017 | 11/2003 |

* cited by examiner

TRANSDUCER-PROTECTOR DEVICE FOR MEDICAL APPARATUS

CROSS-REFERENCE TO RELATED APPLICATIONS

This application claims the benefit of priority of U.S. provisional application No. 60/522,627, filed Oct. 21, 2004, and Italian patent application No. MO2004A000156, filed Jun. 22, 2004, both of which are incorporated herein by reference in their entirety.

BACKGROUND OF THE INVENTION

The invention relates to a transducer-protector device for medical apparatus, useful in particular for protecting medical apparatus from contamination by infectious agents.

Specifically, though not exclusively, the invention can be advantageously applied in an apparatus for extracorporeal blood treatment, in particular a dialysis machine for treatment of kidney failure.

In particular, the invention relates to a transducer-protector device comprising a hollow housing body having two opposite openings, one for communication with an extracorporeal circuit and the other for communication with an operative unit of the medical apparatus, for example a device for measuring pressure in the extracorporeal circuit. The device comprises a barrier, in the form of a membrane, arranged in the housing body between the two openings.

The device of the invention functions both as a transducer, being able to transmit the pressure from one opening to the other without determining any practically relevant drop in pressure, and as an aseptic barrier which protects the medical apparatus from infectious agents originating from the patient.

The prior art comprises various transducer-protector devices of the above-indicated type, described for example in U.S. Pat. No. 4,314,480, EP 0 652 018, U.S. Pat. Nos. 5,500, 003, 6,086,762, 6,506,237 and EP 1 097 725.

These known devices, which are also commonly called "blood-catchers", comprise a hollow housing body having two opposite openings, a membrane housed in the hollow body between the two openings, two opposite tubular connectors, one in fluid communication with a side of the membrane and the other in communication with the other side of the membrane. One of the two tubular connectors is destined to be connected to a fluid line of an extracorporeal blood fluid transport line. The other tubular connector is destined to be connected to a fluid line of an operative unit of a medical apparatus. This medical unit usually comprises a pressure gauge for detecting the pressure within the extracorporeal circuit.

The membrane, which is hydrophobic, defines an anti-contamination barrier which is gas-permeable. The two tubular connectors are in reciprocal gas communication through a fluid pathway comprising the internal cavity of the hollow housing body, while remaining septically insulated one from another along the fluid pathway, thanks to the hydrophobic membrane.

In this way the device allows transmission of the pressure from the fluid-transporting extracorporeal circuit to the pressure gauge, without any significant load loss, while at the same time protecting the operators, the medical apparatus and the surrounding environment, from the risk of contamination by pathogens originating from the fluid running in the extracorporeal circuit. The device can also protect the extracorporeal circuit, and therefore the patient, from the intrusion of extraneous bodies coming from the medical apparatus (dialysis machine).

The hollow housing body normally comprises a pair of half-shells made of a rigid plastic material (for example PETG, PP or PE) joined together by ultrasonic welding. A peripheral edge of the hydrophobic protective membrane (for example made of PTFE) is interpositioned between the two half-shells and held solidly in position there.

A first half-shell bears a first connector which is destined to connect solidly and fluid-sealedly with a flexible tube of the service line in fluid communication with a blood chamber of the extracorporeal circuit. Normally the first half-shell is made in a single piece with the first connector.

The second half-shell bears a second connector which is destined for solid fluid-sealed connection with a male seating situated on the dialysis machine and connected in turn to the pressure gauge. The second connector is generally a female Luer connector made in a single piece of rigid plastic with the second half-shell.

One of the problems of transducer-protector devices of this type is the risk of kinking of the flexible tube which is connected to the first connector and which leads to the blood chamber. Both the transducer-protector device and the blood chamber are positioned on the dialysis machine in predetermined zones and with predetermined and obligated arrangements and orientation. The flexible tube, in order to join up the transducer-protector device and the blood chamber, can be forced to follow a curved pathway, with sometimes changes of direction through relatively narrow angles and the consequent risk of kinking and therefore occlusion of the tube.

A further drawback is that there is a certain degree of difficulty in coupling the device to the seating on the machine, due in part to the rigidity of the device itself.

To obviate these drawbacks the prior art comprises a transducer-protector device having a part which is deformable in a transversal direction to the longitudinal axis of the actual device. The deformable part, which comprises the second female Luer connector, is manufactured in an elastically-deformable material (for example soft PVC), separately from the second half-shell, and is subsequently joined to the second half-shell, for example by gluing using cyclohexanone or another coupling system. The transversal deformability of the soft part made of PVC enables a flexion of the transducer-protector device and reduces the risk of kinking of the flexible tube, easing the coupling maneuver of the machine device.

A drawback of the above-described solution is however its complex build, since it is necessary to manufacture and assemble an extra part. Furthermore, the presence of a further coupling zone, constituted by the gluing zone between the PVC female Luer connector and the rigid-plastic half shell, increases the risk of seal loss which, in this case, might lead to errors or loss of pressure gauge reading.

SUMMARY OF THE INVENTION

The main aim of the present invention is to provide a solution to the above-described limitations and drawbacks of the prior art.

An advantage of the invention is that it provides a transducer-protector device for medical apparatus which is constructionally simple and economical.

A further advantage of the invention is that it provides a transducer-protector device which is rapidly and easily couplable with a machine for extracorporeal blood treatment.

A further advantage is that it provides a transducer-protector device for medical apparatus which reduces the risk of kinking of the flexible fluid-transport tubes coupled thereto.

A still further advantage is that the invention provides a device which is capable of flexing elastically to take on a working configuration which is adaptable to the external elements to which it is coupled.

A further aim of the invention is to make available a connector for fluid-transport tubes which is constructionally simple and economical and which is provided with flexibility, in particular in a transversal direction to a longitudinal axis of the connector.

These aims and advantages and more besides are all attained by the present invention, as it is characterized in one or more of the appended claims.

Further characteristics and advantages of the invention will better emerge from the detailed description that follows of at least one preferred embodiment of the invention, illustrated purely by way of non-limiting example in the accompanying figures of the drawings.

BRIEF DESCRIPTION OF THE DRAWINGS

A description will now follow, with reference to the accompanying figures of the drawings, which are provided purely by way of example and are therefore non-limiting, and in which.

DETAILED DESCRIPTION

Figure 1:
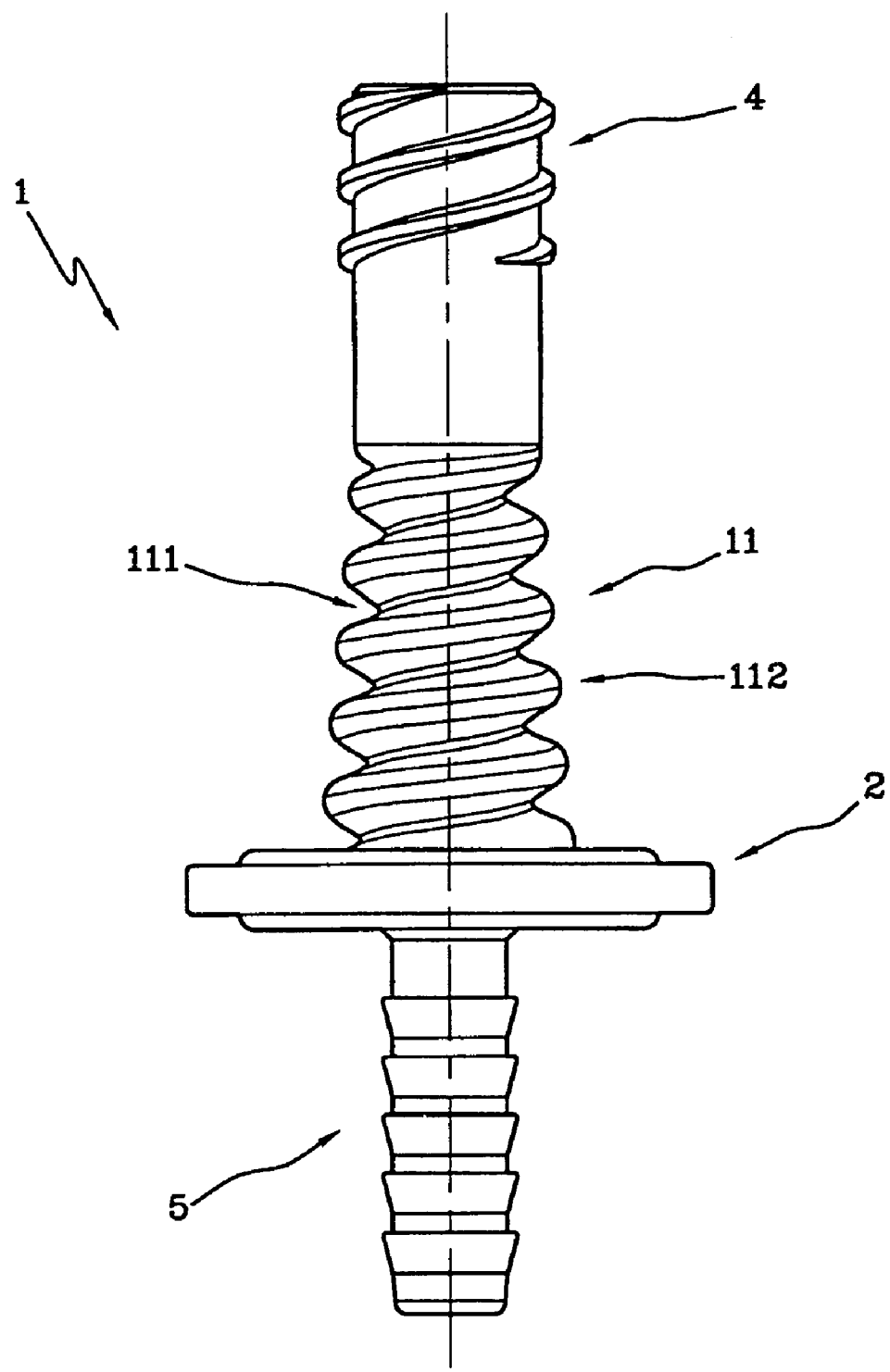
FIG. 1 is a side view of the transducer-protector device of the invention.

Legend
1 Transducer-protector device
2 Housing
2a First half-shell
2b Second half-shell
3 Membrane
4 First connection port
5 Second connection port
6 Male counter-connector
7 Front panel
8 Extracorporeal blood circuit
9 Service line tube
10 Blood chamber
11 Deformable member
111 First fold line
112 Second fold line With reference to the figures of the drawings, 1 denotes in its entirety a transducer-protector device for medical apparatus comprising a housing 2 defining a cavity. The cavity exhibits at least two openings, distanced one from another. In the specific embodiment the openings are coaxial and opposite.

A membrane 3 is contained within the cavity and defines a gas-permeable anti-contamination barrier arranged between the two openings. A first side of the membrane 3 is in communication with and faces an opening of the cavity, while the opposite side of the membrane 3 is in communication with and faces the other opening.

Figure 4:
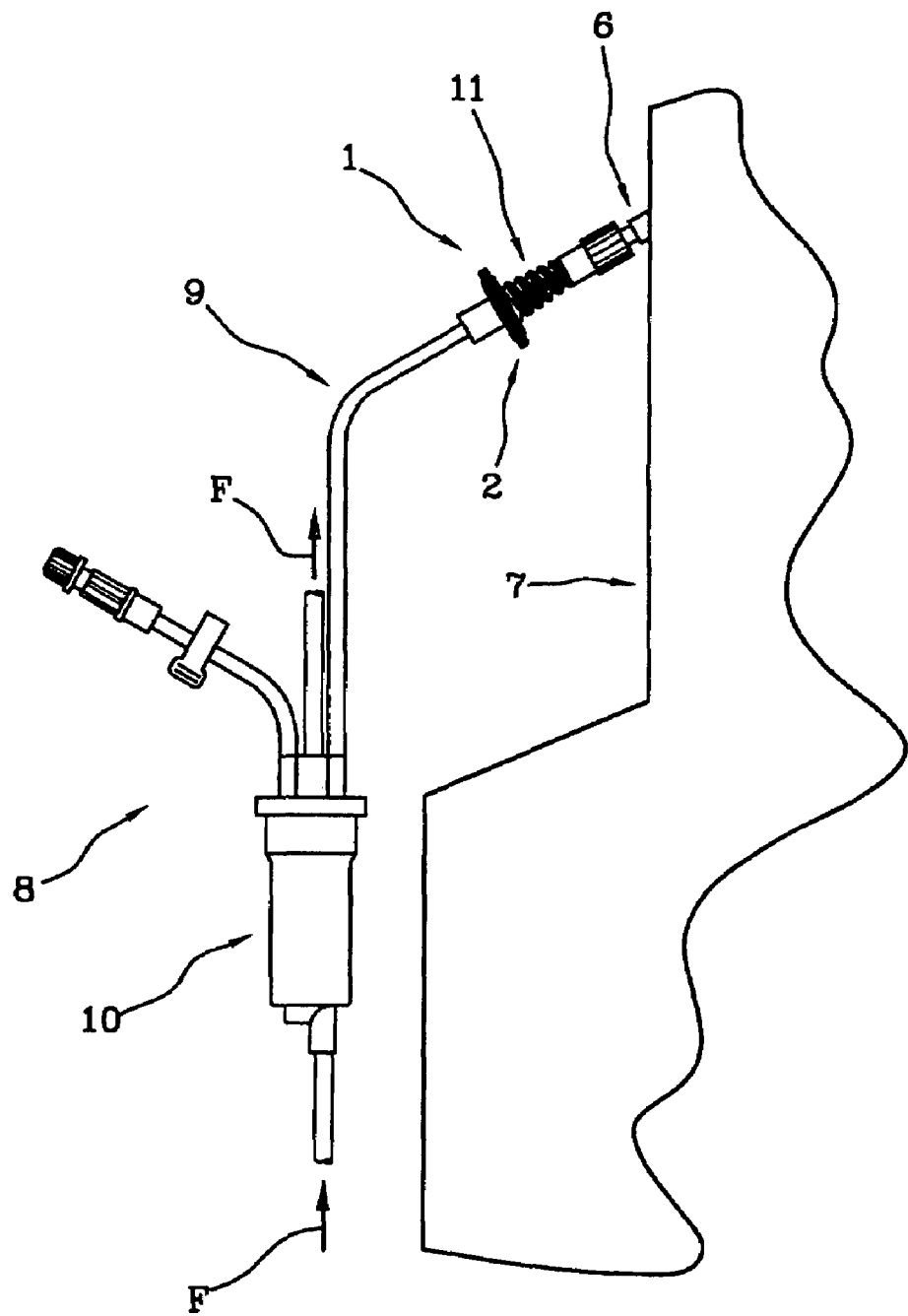
FIG. 4 is a view in vertical elevation of the preceding figures, in a use configuration.

A first connection port 4 is connected to the housing 2 and communicates with a first side of the membrane 3. The first connection port 4 is provided with a female Luer connector, of known type, which is used for coupling with a male Luer counter-connector or seating 6 borne on a front panel 7 of a machine for extracorporeal blood treatment. The machine is, in the specific case, a dialysis machine for performing one or more of the following treatments: hemodialysis, hemofiltration, pure ultrafiltration, hemodiafiltration, therapeutic plasma exchange. The male counter-connector 6 is fluidly connected with a device, of known type and not illustrated, for reading the pressure in an extracorporeal blood circuit 8 to which the transducer-protector device 1 is associated. The extracorporeal circuit 8, which in FIG. 4 is only partially illustrated, is at least provided with an arterial line, which brings the blood taken from a patient's vascular access to a blood treatment device (for example a dialyzer filter), and a venous line which returns the blood once treated to the patient. In FIG. 4 the arrows, indicated by F, indicate the direction of the blood flow along the circuit 8.

A second connection port 5, opposite and coaxial to the first connection port 4, is connected to the housing 2 and communicates with the second side of the membrane.

The second connection port 5 is provided with a tubular connector of known type, which externally bears a plurality of annular projections, axially distanced one from another, which tubular connector is destined for connection with an end of a flexible tube 9 which, at an opposite end thereof, is connected to a blood chamber 10 of the extracorporeal circuit 8. The solid connection, which is also fluid-sealed, between the flexible tube 9 and the connector of the second connection port 5, is of known type.

The first connection port 4 has a longitudinal axis which coincides with a longitudinal axis of the second connection port 5.

Figure 2:
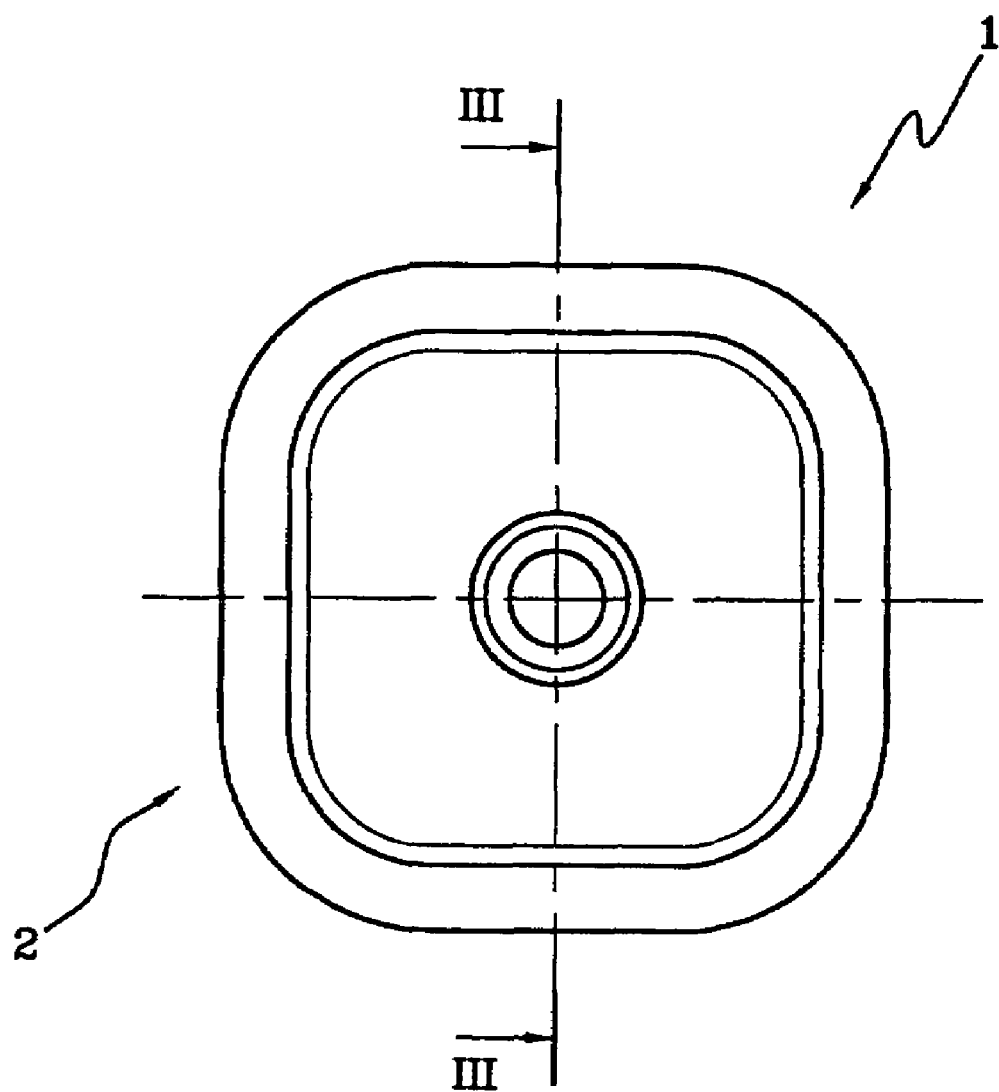
FIG. 2 is a view from below of FIG. 1.
Figure 3:
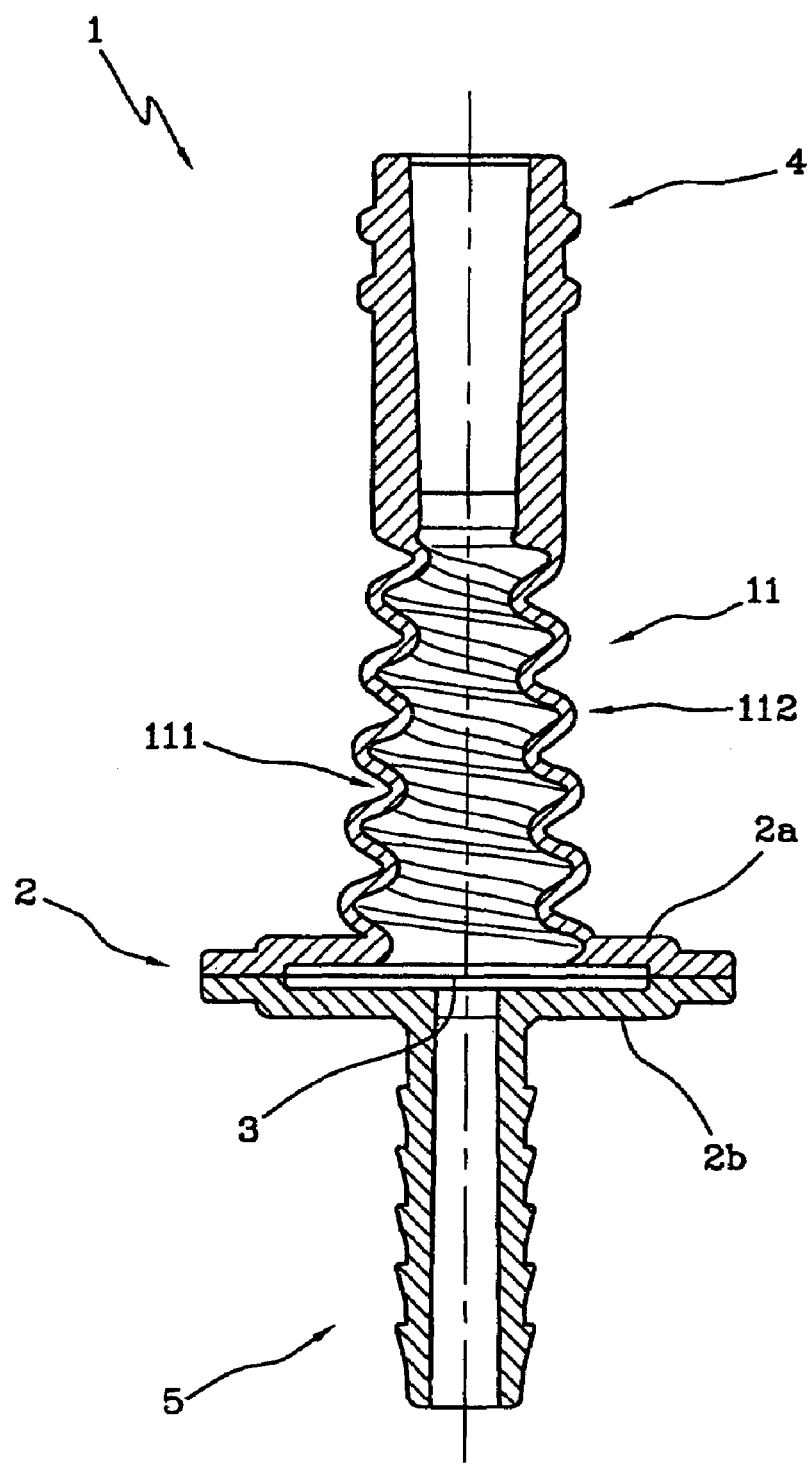
FIG. 3 is a section according to line III-III of FIG. 2.

The housing 2 has, in plan view (as can be seen in FIG. 2), an essentially square shape with rounded corners, as does the membrane 3. Both the housing 2 and the membrane 3 have a common central axis, perpendicular to both, which coincides with the longitudinal axis of the two connection ports 4 and 5.

The transducer-protector device 1 essentially has the function of providing an anti-contamination protection barrier arranged between the extracorporeal blood circuit and the machine for extracorporeal blood treatment. The fact that the membrane 3 is gas-permeable means that the machine can measure the pressure in the circuit.

The membrane 3, which has the function of forming a gas-permeable barrier predisposed between the two openings of the internal cavity of the housing 2, is made of a hydrophobic material, such as for example PTFE.

The housing 2 comprises two half-shells 2a and 2b, each having a flanged part which is square with rounded edges, which flanged part traps a periphery of the membrane 3, which is also square with rounded edges. The half-shells 2a and 2b are solidly joined together, for example by ultrasonic welding along a square-shaped weld line with rounded edges. The annular joint zone between the half-shells 2a and 2b is also the zone in which the membrane 3 periphery is interpositioned between the half-shells 2a and 2b and is attached solidly to the housing 2.

The flanged two half-shells 2a and 2b are made of a plastic material which is suitable for ultrasonic welding, such as, for example, PETG or PP or PE.

A deformable member 11 is arranged between the housing 2 where the membrane 3 is trapped and one of the connection ports 4 or 5, which in the specific embodiment is the first connection port 4.

The deformable member 11 is integrated with at least a part of the housing 2. In the specific embodiment, the deformable member 11 is integrated with the first half-shell 2a.

Further, the deformable member 11 is integrated with at least a part of one of the two connection ports. In the specific embodiment, the deformable member 11 is integrated with the first connection port 4.

The deformable member 11, at least a part of the housing 2, constituted in the specific embodiment by the first half-shell 2a, and at least a part of one of the two connection ports, in the specific embodiment the first connection port 4, are all integrated in a single piece made of a plastic material which can be welded by ultrasonic welding. In the specific embodiment the piece is obtained by injection molding.

The deformable member 11 is made of the same material as the housing 2, which in the specific embodiment is a plastic material susceptible to ultrasonic welding, in order to enable, as mentioned above, a joining of the two half-shells 2a and 2b, as well as a solid, permanent and fluid-sealed union with the hydrophobic membrane 3.

The deformable member 11 comprises a hollow body. An internal zone of the hollow body is in fluid communication with a side of the membrane 3, which in the specific embodiment is the first side fluidly connected with the first connection port 4. The internal zone of the hollow body is in fluid communication with the first connection port 4. In more detail, the deformable member 11 is at least partially tubular in shape. The longitudinal axis of the deformable member 11 coincides with the longitudinal axis of the first connection port 4.

The deformable member 11 has a first end which is connected solidly to the first connection port 4, and a second end which is solidly connected to the housing 2. In the specific embodiment the second end has a larger diameter than the first end. In particular, the deformable member 11 has a mean diameter that grows as it progresses from the first connection port 4 to the housing 2.

The deformable member 11 is conformed and arranged so as to be deformable in at least a transversal direction to the longitudinal axis. In particular, the deformable member 11 is conformed and arranged so as to enable both axial deformations and transversal deformations. In more detail, the deformable member 11 is bellows-conformed. In still greater detail, the deformable member 11 is bellows-conformed and at least partially helical.

Other embodiments, however, can be envisaged, not illustrated, in which the deformable member is differently conformed, for example it can be bellows-shaped in the normal way, i.e. formed by a wall conformed in such a way as to exhibit a plurality of closed annular fold lines (circular or of another closed annular shape), axially distanced one from another, having alternatingly smaller and larger dimensions.

In the specific embodiment, the hollow body forming the deformable member 11 comprises a wall having at least a first fold line 111 which is orbitally extended about a longitudinal axis thereof. In the specific embodiment the first fold line 111 has a helical development. In more detail, the helical first fold line 111 has a variable diameter in an axial direction. In still greater detail, the diameter of the helical first fold line 111 increases in an axial direction as it progresses towards the housing 2. Further, the first fold line 111 is arranged on a concave part of the wall having a concavity thereof facing externally of the hollow body.

The wall of the deformable hollow body further comprises a second fold line 112, also orbitally extended about a longitudinal axis, with a helical development, having a diameter which increases in an axial direction progressing towards the housing 2. The second fold line 112 is arranged on a concave part of the wall, which concave part has a concavity facing internally of the hollow body.

Each of the first fold line 111 and the second fold line 112 serves as a hinge or articulation/joint about which two contiguous portions of the deformable member 11 can move one with respect to the other.

The wall of the hollow body, which is helical-bellows conformed, is provided with two fold lines, developing as helices, which are coaxial, have the same step and are reciprocally staggered by about a half of the step; one of the helices is more internal than the other. The more internal of the helices, having a smaller diameter, is the first fold line 111, while the more external fold line, having a greater diameter, is the second fold line 112. The two fold lines 111 and 112 are arranged on two concave and helically-extending parts of the wall which parts have concavities facing, respectively, externally and internally of the hollow body.

The deformability of the hollow body is mainly caused by bellows-type deformations, constituted by reciprocal rotations of helical portions of wall about the fold lines 111 and 112; the helical portions of wall are defined between one fold line and the other.

The bellows-conformed deformable member 11 is connected to the housing 2 and, in more detail, is integrated with a part of the housing 2.

The hollow body, which is subject to helical bellows deformation, has an internal surface with a helically-extended fold where the second fold line 112 is located, and a helically-extended protuberance where the first fold line 111 is located.

Similarly, the external surface of the hollow body has a helically-extended fold where the first fold line 111 is located, and a helically-extended protuberance where the second fold line 112 is located.

The transducer-protector device 1 is made in three pieces which are assembled together during a single operation of ultrasonic welding. The three pieces are constituted, in the specific embodiment, as follows: a first piece, which is manufactured by injection molding and which integrates the first connection port 4, the deformable body 11 and the first half-shell 2a; a second piece, also made by injection molding and which integrates the second connection port 5 and the second half-shell 2b; and a third piece constituted by the protective gas-permeable membrane 3.

The helical shape of the bellows-deformable body renders the injection molding of the first piece easier. The internal surface of the deformable body can be formed using, for example, a forming core which is provided with a helical external surface. The forming core can be extracted from the formed piece by a simple unscrewing movement which combines a rotary movement with an axial one.

The transducer-protector device 1 is similar to a pipe union, comprising at least a deformable helical bellows-conformed part. This bellows-conformed part gives the connector a certain degree of deformability, both in axial and in transversal (to the axis) directions. The helical shape of the bellows enables, as described, it to be very simply formed by injection molding of plastic material, using, during molding, a helical core which, after forming, is easily extracted from the piece, for example by an unscrewing motion to detach it from the internal helical shape of the formed piece. The helical bellows can also be made using a relatively rigid plastic material (such as for example PETG, PP or PE), which is susceptible to ultrasonic welding. The bellows-shaped deformable member as described above in relation to the transducer-protector device 1 can also be used for other types of tube connections, in particular for plastic connectors applicable to fluid transport lines for medical use.

In the present case, the transducer-protector device 1 is applied in a fluid transport line for medical use constituted in particular by a service line for pressure reading in a blood chamber of an extracorporeal blood circuit, especially for dialysis. This service line, which comprises a helical bellows-shaped deformable part, is coupled to a machine for extracorporeal blood treatment, which in the specific case described is a dialysis machine comprising at least one operative unit, which in the specific case is a pressure gauge, operatively associable to the extracorporeal blood circuit.

The apparatus for extracorporeal blood treatment, which comprises the machine and the circuit, is predisposed for carrying out one or more of the following treatments: hemodialysis, hemofiltration, pure ultrafiltration, hemodiafiltration, therapeutic plasma exchange.

The invention claimed is:

1. A transducer-protector device comprising:
   a housing defining a cavity;
   a membrane defining in said cavity a gas-permeable anti-contamination barrier;
   a first connection port associated to said housing and communicating with a first side of said membrane; and
   a deformable member arranged between said housing and said first connection port, said deformable member comprising a hollow body, said hollow body comprising wall having at least a first fold line: said first fold line extending orbitally about a longitudinal axis thereof.

2. The device of claim 1, wherein said deformable member is made in a single piece with at least a part of said housing.

3. The device of claim 1, wherein said deformable member is made in a single piece with at least a part of said first connection port.

4. The device of claim 1, wherein said deformable member, at least a part of said housing, and at least a part of said first connection port are integrated in a single piece.

5. The device of claim 1, wherein said housing comprises two half-shells which entrap and hold a periphery of said membrane, a first of said half-shells being made in a single piece with said deformable member.

6. The device of claim 1, wherein said deformable member is at least partially tubular.

7. The device of claim 1, wherein said first connection port has a longitudinal axis, and wherein said deformable member is conformed and arranged such as to be deformable in at least a transversal direction to said longitudinal axis.

8. The device of claim 1, wherein at least an internal zone of said hollow body is in fluid communication with said first side of said membrane.

9. The device of claim 1, wherein said first fold line is helically extended.

10. The device of claim 9, wherein said helical first fold line has a diameter which is variable in an axial direction thereof.

11. The device of claim 10, wherein the diameter of said first fold line increases in an axial direction thereof in a direction thereof progressing towards said housing.

12. The device of claim 1, wherein said first fold line is arranged on a concave part of said wall which concave part has a concavity thereof facing externally of said hollow body.

13. The device of claim 1, wherein said hollow body comprises a wall having at least a second fold line.

14. The device of claim 13, wherein said second fold line is extended orbitally about a longitudinal axis thereof.

15. The device of claim 14, wherein said second fold line is helically extended.

16. The device of claim 15, wherein said helical second fold line has a diameter which is variable in an axial direction thereof.

17. The device of claim 16, wherein the diameter of the second fold line increases in an axial direction thereof in a direction progressing towards said housing.

18. The device of claim 13, wherein said second fold line is arranged on a concave part of said wall which concave part has a concavity thereof facing internally of said hollow body.

19. The device of claim 1, wherein said hollow body comprises a wall having at least two fold lines which are helically extended and coaxial one to another.

20. The device of claim 19, wherein said at least two fold lines have a same step.

21. The device of claim 19, wherein said at least two fold lines have different diameters.

22. The device of claim 19, wherein said at least two fold lines are arranged on two concave parts of said wall having concavities thereof facing, respectively, one externally and one internally of said hollow body.

23. The device of claim 1, wherein said deformable member is bellows-conformed.

24. The device of claim 1, wherein said deformable member is bellows-conformed and is at least partially helical.

25. The device of claim 1, wherein said deformable member has a first end which is connected to said first connection port and a second end which is connected to said housing, said second end having a greater diameter than said first end.

26. The device of claim 1, wherein said deformable member has an internal surface which exhibits a fold at least partially helically extended.

27. The device of claim 1, wherein said deformable member has an external surface which exhibits a fold at least partially helically extended.

28. The device of claim 1, wherein said deformable member is made of a same material as at least a part of said housing.

29. The device of claim 1, wherein said deformable member is made of a plastic material which is susceptible to injection molding.

30. The device of claim 1, wherein said deformable member is made of a plastic material which can be welded by ultrasonic welding.

31. The device of claim 1, comprising a second connection port, associated to said housing and communicating with a second side of said membrane.

32. The device of claim 1, wherein said membrane is constrained to said housing.

33. A transducer-protector device comprising:
   a housing defining a cavity with at least two reciprocally-distanced openings;
   a membrane defining in said cavity a gas-permeable anti-contamination barrier and arranged in said cavity between the two openings;
   a bellows-conformed deformable member connected to said housing.

34. The device of claim 33, comprising a first connection port associated to said housing and communicating with a first side of said membrane, said deformable member being arranged between said housing and said first connection port.

35. A fluid transport line for medical use, comprising a transducer-protector device according to claim 1.

36. An extracorporeal blood circuit comprising a fluid transport line provided with a transducer-protector device according to claim 1.

37. An apparatus for extracorporeal blood treatment comprising at least one operative unit which is operatively associable to an extracorporeal blood circuit, and at least one extracorporeal blood circuit provided with a transducer-protector device according to claim 1.

38. The apparatus of claim 37, wherein said operative unit comprises a system for gauging a pressure in the extracorporeal circuit.

39. The apparatus of claim 37, predisposed to perform one or more of following treatments: hemodialysis, hemofiltration, hemodiafiltration, pure ultrafiltration, therapeutic plasma exchange.

40. A transducer-protector device comprising:
a housing defining a cavity;
a membrane defining in said cavity a gas-permeable anti-contamination barrier;
a first connection port associated to said housing and communicating with a first side of said membrane; and
a deformable member arranged between said housing and said first connection port, said deformable member being bellows-conformed.

41. A transducer-protector device comprising:
a housing defining a cavity;
a membrane defining in said cavity a gas-permeable anti-contamination barrier;
a first connection port associated to said housing and communicating with a first side of said membrane; and
a deformable member arranged between said housing and said first connection port, said deformable member comprising a hollow body, said hollow body comprising a wall having at least a first fold line, said first fold line extending orbitally and helically about a longitudinal axis thereof.

42. A transducer-protector device comprising:
a housing defining a cavity;
a membrane defining in said cavity a gas-permeable anti-contamination barrier;
a first connection port associated to said housing and communicating with a first side of said membrane; and
a deformable member arranged between said housing and said first connection port, said deformable member comprising a hollow body, said hollow body comprising a wall having at least a first fold line, said first fold line extending orbitally and helically about a longitudinal axis thereof,
wherein said hollow body comprises a wall having at least a second fold line, said second fold line extending orbitally and helically about a longitudinal axis thereof.

43. A transducer-protector device comprising:
a housing defining a cavity;
a membrane defining in said cavity a gas-permeable anti-contamination barrier;
a first connection port associated to said housing and communicating with a first side of said membrane; and
a deformable member arranged between said housing and said first connection port, said deformable member comprising a hollow body, said hollow body comprising a wall having at least two fold lines that are helically extended and coaxial one to another.

* * * * *